US00PP19429P3

(12) United States Plant Patent
Maranto

(10) Patent No.: US PP19,429 P3
(45) Date of Patent: Nov. 4, 2008

(54) GRAPEVINE NAMED 'CARA SEEDLESS'

(50) Latin Name: *Vitis vinifera*
Varietal Denomination: Cara Seedless

(75) Inventor: Joseph Maranto, Bakersfield, CA (US)

(73) Assignee: Anton Caratan & Son, Delano, CA (US)

( * ) Notice: Subject to any disclaimer, the term of this patent is extended or adjusted under 35 U.S.C. 154(b) by 0 days.

(21) Appl. No.: 11/711,771

(22) Filed: Feb. 28, 2007

(65) Prior Publication Data

US 2008/0209603 P1 Aug. 28, 2008

(51) Int. Cl.
*A01H 5/00* (2006.01)

(52) U.S. Cl. ..... Plt./205

(58) Field of Classification Search ..... Plt./205
See application file for complete search history.

*Primary Examiner*—Kent L. Bell
*Assistant Examiner*—June Hwu
(74) *Attorney, Agent, or Firm*—Buchanan Ingersoll & Rooney PC

(57) ABSTRACT

A new and distinct variety of grapevine is provided which abundantly forms attractive medium-to-large seedless berries having a dark eggplant skin coloration in compact clusters. The fruit displays a sweet crisp flavor and is firm in texture. The fruit commonly is ready for harvest during late September to early October in the San Joaquin Valley of Central California, U.S.A., and displays good eating qualities as a table grape. The fruit firmness renders the fruit well amenable for handling, shipping, and storage.

1 Drawing Sheet

Figure 1:
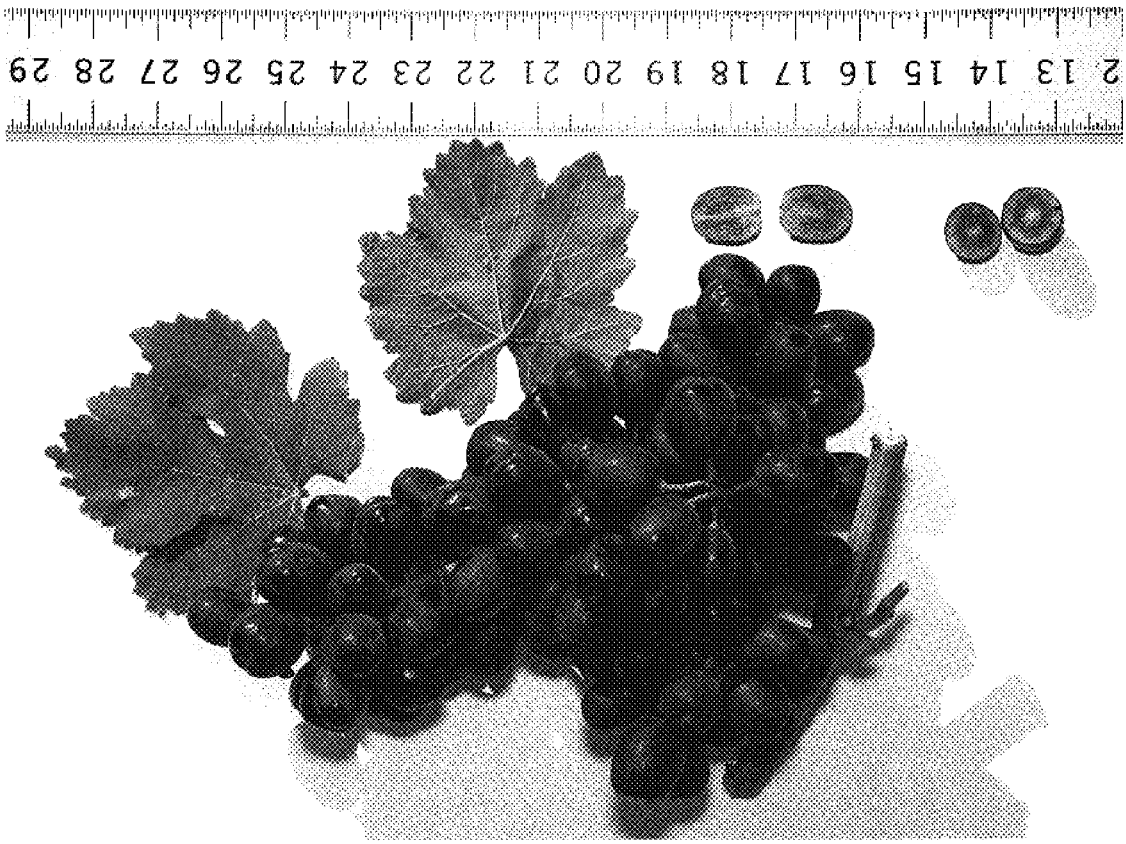

Botanical/commercial classification: *Vitis vinifera*/Grapevine.
Varietal denomination: cv. Cara Seedless.

Background of the New Variety

New grapevine varieties are being sought which display a combination of outstanding characteristics in areas such as vigor, productivity, and resistance to diseases and pests. Characteristics such as fruit size, coloration, flavor, taste, and seedless nature of the fruit, also are of importance when evaluating new varieties of grape plants.

The new variety of *Vitis vinifera* was created by artificial pollination during the course of a grapevine breeding program wherein two parents were crossed which previously had been studied in the hope that they would contribute the desired characteristics. Such breeding program was initiated during 1992 near Delano in the San Joaquin Valley of Central California, U.S.A. The cross that resulted in the creation of the new variety of the present invention was made in 1993. The female parent (i.e. the seed parent) of the new variety was the 'Ribier' seeded grape variety (non-patented in the United States). The 'Ribier' variety originated in France and sometimes is known as the 'Alphonse Lavallee' variety. The male parent (i.e. the pollen parent) of the new variety was the 'Crimson' seedless grape variety (non-patented in the United States). The 'Crimson' male parent was released by the U.S.D.A. at Fresno, Calif. U.S.A., during 1989 and was formed by the cross of the 'Emperor' variety (non-patented in the United States) and an unreleased seedling named 'C33-1-99' (non-patented in the United States).

The parentage of the new variety can be summarized as follows:

*Ribier* × *'Crimson'*.

The seeds resulting from the above pollination were sown and small seedling plants were obtained which were physically and biologically different from each other. The resulting seedling plants were evaluated in detail and the new variety of the present invention was selected and was initially designated 'ACS V(1-5) R32B'.

It was found that the new grapevine of the present invention possesses the following combination of characteristics:

(a) forms attractive medium-to-large seedless berries having a dark eggplant skin coloration in compact clusters which display a sweet crisp flavor, (b) commonly bears fruit during late September to early October in the San Joaquin Valley of Central California, U.S.A., and (c) bears fruit that is firm and is well amenable for storage, handling, and shipping.

The new variety is well adapted for growing under the soil and climate conditions of the San Joaquin Valley of Central California, U.S.A., where a late spring frost is rare and minimum and maximum temperatures commonly range from approximately 25 to 108° F. The new variety during observations to date has displayed no visible disease, and has displayed an ability to well resist cold, drought, heat and wind. The fruit of the new variety has been found to display excellent handling and shipping qualities combined with desirable dessert eating qualities.

The new variety of the present invention can be readily distinguished form its ancestors. More specifically, the 'Ribier' parent forms berries which possess seeds and which are ready for harvest a few weeks earlier than the new variety, and the 'Crimson' variety forms smaller berries which display a dissimilar rose pink coloration.

The new variety of the present invention additionally can be readily distinguished from the 'Summer Royal' variety (non-patented in the United States), and the 'Autumn Royal' variety (non-patented in the United States). Unlike the new variety the grapes of the 'Summer Royal' variety commonly turn black by harvest time and have a tendency to crack. Also, the fruit of the 'Autumn Royal' variety differs from that of the new variety and is purple to black in appearance and ripens during mid-October when grown in the San Joaquin Valley of Central California, U.S.A.

The new variety of the present invention has been found to undergo asexual propagation beginning in 1998 near Delano in the San Joaquin Valley of Central California, U.S.A. by grafting on mature 'Thompson Seedless' rootstock (non-patented in the United States). Such asexual propagation has been conducted thereafter in successive years through 2006, and has shown that the characteristics of the new variety are strictly transmissible from one generation to another. Accordingly, the new variety undergoes asexual propagation in a true to type manner.

Vines of the new variety optionally can be sprayed with gibberellic acid, for example at approximately 80 to 90 percent bloom to reduce berry set and sprayed again at approximately 2 weeks after full bloom. Truck girdles sometimes applied with table grape varieties to increase berry weight are not needed with the new variety.

The new variety has been named 'Cara Seedless'.

BRIEF DESCRIPTION OF THE PHOTOGRAPH

The accompanying photograph shows as nearly true as it is reasonably possible to make in color illustration of this character typical specimens of the new variety. The photograph includes a typical cluster of the attractive grapes, upper and under surfaces of the leaves, and berries that are transversely and longitudinally sectioned in order to reveal the flesh which lacks seeds.

Dimensions in centimeters are shown at the top of the photograph for comparative purposes.

DETAILED DESCRIPTION

The chart used in the identification of colors is the Dictionary of Color by A. Maerz and M. Rea Paul (1930). Common color terms are to be accorded their ordinary dictionary significance. The description is based on the observation of plants approximately eight years following asexual propagation and growth on 'Thompson Seedless' rootstock outdoors near San Joaquin Valley of Central California, U.S.A.

Vine:

*Vigor.*—Exceeds that of its 'Ribier' and 'Crimson' parental varieties and forms a thick canopy.

*Productive capacity.*—Very productive.

*Trunk.*—Slender, includes long split strips, and eight years after grafting the diameter commonly is approximately 3.7 inches (approximately 94 mm) measured 1 foot above the ground.

*Bark color.*—Reddish brown (8-H-11) Congo, and (7-C-11) Zuni Brown underbark.

Cane length. —Medium, and commonly approximately 6 feet (approximately 1.8 m).

*Cane width.*—Medium, and commonly approximately 0.5 inch (approximately 13 mm) at node.

*Nodes.*—Generally round in configuration, and commonly spaced at a distance of 3 to 4 inches (approximately 76 to 102 mm).

*Shoot configuration.*—Substantially circular, and approximately 0.7 mm in diameter.

*Shoot color.*—Light green (30-D-3).

*Shoot texture.*—Glossy.

*Tendril length.*—Commonly approximately 4 to 5 inches (approximately 102 to 127 mm).

*Tendril form.*—Very thin, bifurcated and trifurcated, and few in number.

*Tendril color.*—Biscay green (21-K-5).

*Tendril texture.*—Smooth.

*Bud shape.*—Pointed conical.

*Bud length.*—Commonly approximately 6 mm.

*Bud width.*—Commonly approximately 6 mm.

*Bud break.*—Commonly at the end of March or early April at the specified location.

Leaves:

*Size.*—Generally medium.

*Density.*—Heavly.

*Length.*—Approximately 4 to 5 inches (approximately 102 to 127 mm) on average for a mature leaf.

*Color.*—Dark green (24-A-11) Mountain green forest on the ventral (upper) surface, and light green (23-H-2) on the dorsal (under) surface. As with other grape varieties, the ventral leaf surfaces which are more exposed to the sun and other environmental factors commonly are darker in coloration than the dorsal leaf surfaces.

*Texture.*—Smooth on the dorsal surface, and glabrous on the ventral surface.

*Petiole length.*—Commonly approximately 3 to 5 inches (approximately 76 to 127 mm).

*Petiole diameter.*—Commonly approximately 4 mm.

*Petiole sinus.*—U-shaped to V-shaped, and occasionally overlapping.

*Petiole color.*—Light green (23-L-7).

*Lobe.*—Primarily five-pointed.

*Color midrib.*—Grape green (21-J-1).

*Margins.*—Generally serrate with irregular teeth, commonly approximately 10 to 12 teeth per lobe, and approximately 45 to 60 teeth on entire leaf.

Flowers:

*Date of bloom.*—Commonly approximately May 5th to 10th at the specified location.

*Date of full bloom.*—Commonly approximately May 15th to 20th at the specified location.

*Type.*—Fertile.

*Shape.*—Pear-shaped prior to opening.

*Size.*—Commonly approximately 0.4 cm in diameter on average at full bloom.

Location. —Primarily at the 2nd to 4th node from the base on a spur.

*Petals.*—Five in number, open from the bottom to the top, and light green (23-L-7) in coloration.

*Sepals.*—Five in number, and commonly poorly developed.

*Stamen.*—Six in number, approximately 1.6 mm in length, and upright and diverging.

*Pollen.*—Abundant, and yellow (9-L-4) Sunflower dandelion in coloration.

*Pistil.*—One in number, produces a liquid to hold pollen to achieve germination.

*Filaments.*—Substantially straight, approximately 2 mm in length, and green (22-L-4) Calla green in coloration.

*Calyptra.*—Commonly light green (23-L-7) in coloration.

*Peduncle.*—Commonly approximately 34 mm in length on average, and alpine green (31-C-9) in coloration.

Fruit:

*Time.*—Commonly ripe for commercial harvesting and shipment during late September to early October at the specified location, a few weeks later than the 'Ribier' variety, and at about the same time as the 'Crimson' variety.

*Berry size.*—Medium to large.

*Berry form.*—Mostly uniform.

*Berry shape.*—Ovoid to ellipsoidal.

*Berry length.*—Commonly approximately 0.9 to 1 inch (approximately 23 to 26 mm).

*Berry width.*—Commonly approximately 0.7 to 0.8 inch (approximately 18 to 20 mm).

*Berry weight.*—Commonly approximately 6 to 7 grams on average.

*Berry number.*—Commonly approximately 100 to 125 per cluster on average.

*Berry weight.*—Commonly approximately 6 to 7 grams on average.

*Cluster form.*—Commonly conical shouldered, and compact.

*Cluster weight.*—Commonly approximately 500 to 750 grams on average.

*Solids.*—15 percent sugar on Jul. 31, 2006, 17 percent sugar on Aug. 22, 2006, 18 percent sugar on Sep. 8, 2006, and 19 percent sugar on Sep. 15, 2006.

*Acidity.*—Approximately 0.33 percent tritrable acidity during mid-September.

*Sugar/acid ratio.*—Approximately 57.5.

*Juice pH.*—Approximately 3.97.

*Seeds.*—Seedless, with an occasional few small traces of seeds.

*Capstem.*—Strong with long chalaza and attached to vascular tissue.

*Pedicel.*—Approximately 0.3 inch to 0.35 inch (approximately 8 to 9 mm) in length.

*Skin texture.*—Very firm.

*Skin cracking.*—No tendency to crack.

*Skin color.*—Dark (48-H-12) Eggplant. Seasonal temperature variations during ripening have not been found to influence color development. An attractive bloom commonly is exhibited on the surface of the grapes.

*Pulp.*—Adheres to skin.

*Lenticels.*—None visible.

*Flesh color.*—Gray (39-C-2).

*Flavor.*—Sweet and crisp.

*Eating quality.*—Good.

*Use.*—Dessert, table grape.

*Keeping quality.*—Very good, after one month in storage, still displays good appearance.

Development:

*Resistance to diseases.*—No disease problem has been observed.

*Resistance to cold.*—Good, performs well in the San Joaquin Valley of Central California, U.S.A. wherein winter temperature sometimes drop to approximately 13 to 29° F.

*Resistance to drought.*—Good.

*Resistance to heat.*—Good, performs well in U.S.D.A. Hardiness Zone Nos. 5 and 6 where summer temperatures as high as approximately 105 to 108° F. have been withstood.

*Resistance to wind.*—Good.

*Shipping and handling.*—Excellent.

The 'Cara Seedless' variety has not been observed under all possible environmental conditions to date. Accordingly, it is possible that the phenotypic expression may vary somewhat with changes in length intensity and duration, cultural practices, and other environmental conditions.

I claim:

1. A new distinct grape plant characterized by the following combination of characteristics:

(a) forms attractive medium-to-large seedless berries having a dark eggplant skin coloration in compact clusters which display a sweet crisp flavor, (b) commonly bears fruit during late September to early October in the San Joaquin Valley of Central California, U.S.A., and (c) bears fruit that is firm and is well amenable for storage, handling, and shipping;

substantially as herein shown and described.

* * * * *